United States Patent [19]
Schwartz

[11] Patent Number: 5,902,261
[45] Date of Patent: May 11, 1999

[54] METHOD AND APPARATUS FOR PREFABRICATED RETRACTING ELEVATING SCAPULOTHORACIC ORTHOSIS

[75] Inventor: L. Matthew Schwartz, Philadelphia, Pa.

[73] Assignee: Albert Einstein Healthcare Network, Philadelphia, Pa.

[21] Appl. No.: 08/847,170

[22] Filed: Apr. 30, 1997

[51] Int. Cl.$^6$ .............................. A61F 13/00; A61F 5/37
[52] U.S. Cl. .............................. 602/61; 602/60; 128/874
[58] Field of Search .............................. 602/2, 4, 5, 20, 602/61, 62; 128/869, 874, 877, DIG. 19; 2/44, 45

[56] References Cited

U.S. PATENT DOCUMENTS

| | | | |
|---|---|---|---|
| 559,024 | 4/1896 | Bessing | 2/44 |
| 1,336,695 | 4/1920 | Gromes . | |
| 2,543,847 | 3/1951 | Hallstedt . | |
| 3,739,772 | 6/1973 | Ennis | 128/80 |
| 3,888,244 | 6/1975 | Lebold | 128/77 |
| 4,091,808 | 5/1978 | Nelson | 128/133 |
| 4,252,112 | 2/1981 | Joyce | 128/80 |
| 4,483,336 | 11/1984 | Deitch | 128/94 |
| 4,598,703 | 7/1986 | Lindemann | 128/94 |
| 4,641,882 | 2/1987 | Young | 297/183 |
| 4,785,803 | 11/1988 | Benckhuijsen | 602/20 |
| 4,800,593 | 1/1989 | Ruffner | 2/44 |
| 4,940,066 | 7/1990 | Santilli et al. | 128/882 |
| 4,971,073 | 11/1990 | Schneider | 128/869 X |
| 5,230,700 | 7/1993 | Humbert et al. | 602/23 |
| 5,388,274 | 2/1995 | Glover et al. | 602/20 X |
| 5,609,569 | 3/1997 | Oflenhartz | 602/62 X |
| 5,628,725 | 5/1997 | Ostergard | 602/62 |

OTHER PUBLICATIONS

Neal, M.R. & Williamson, J. "Collar Sling for Bilateral Should Subluxation" *Am. J. Occupational Therapy* vol. 34, No. 6, Jun. 1980, pp. 400–401.

*Primary Examiner*—Richard J. Apley
*Assistant Examiner*—Denise Pothier
*Attorney, Agent, or Firm*—John S. Child, Jr.; Mitchell R. Brustein; Dann, Dorfman, Herrell and Skillman

[57] ABSTRACT

Apparatus for applying force to a patient's upper torso and cervical region, and method for using the same, comprising a pair of panels adapted to fit under the arms of a patient and to cover the patient's chest and back. The panels have edges defining lateral extremities of the panels at the patient's chest and back. A pair of sleeves is provided having tubular portions adapted for receiving the patient's arms therein. The tubular portions have a slit and are adapted for adjustable fitting about the patient's distal biceps. Straps are used for maintaining the panels against the patient's chest. A bulbous disk is provided for contacting the rear of the patient's lower neck and upper back and for applying a spreading force over the patient's neck and back. Straps are connected to front surfaces of the sleeve upper portions and adapted for applying force to the disk and hence to the patient's neck, back, shoulder girdles, and upper extremities. Straps are provided for pulling the panels towards one another across the patient's back.

18 Claims, 7 Drawing Sheets

METHOD AND APPARATUS FOR PREFABRICATED RETRACTING ELEVATING SCAPULOTHORACIC ORTHOSIS

FIELD OF THE INVENTION

This invention relates to methods and apparatus in the field of Orthotics which is a branch of mechanical and medical science dealing with the support and bracing of weak or ineffective joints or muscles and is particularly concerned with joints and muscles in the shoulder area of humans.

DESCRIPTION OF THE PRIOR ART

Motion and control of scapulothoracic articulation of the shoulder in a human being is a critical component of normal biomechanics for many upper extremity activities and maintenance of proper posture. Central neurological and peripheral neurological and musculoskeletal impairments can cause muscular dysfunction via contracture or imbalance which leads to pain and disability.

Apparatus for applying force to selected portions of the body in the area of the shoulder are known. The Contoured Clavicle Strap is disclosed in a catalogue distributed by Sammons and constitutes molded "D" shaped straps designed to conform to the axilla and not impinge on the brachial artery or nerve. The Contoured Clavicle Strap product is made of a breathable polyurethane form covered with a non-allergenic stockinette using Velcro closures which are pressure sensitive to effectuate closing.

Another prior art apparatus is the product sold under the trademark Posture Corrector by the Saunders Group. Both the Contoured Clavicle Strap and the Posture Corrector passively retract or remind the wearer to retract both scapulothoracic articulations to decrease shoulder girdle pain and dysfunction caused by muscle and/or nerve dysfunction due to or causing static protraction. Neither the Contoured Clavicle Strap nor the Posture Corrector provide an elevation moment and hence do not provide symptomatic control of a depressed scapulothoracic articulation. Additionally, both the Contoured Clavicle Strap and the Posture Corrector are difficult for the patient to put on and to take off independently. Finally, both of these products result in axillary impingement.

An upper arm support sling is available from Rolyan as the hemi-arm sling and is promoted as providing unilateral anti-subluxation support. The Rolyan hemi sling is intended to position the head of the humerus in the glenoid fossa and the scapula in retraction. The Rolyan hemi-arm sling is disclosed in U.S. Pat. No. 4,598,703.

An advantage of the Rolyan hemi-arm sling is that it decreases inferior glenohumeral subluxation and permits free distal upper extremity function. The Rolyan hemi-arm sling can be used to retract and elevate, to a minimal or moderate degree, a protracted and/or depressed scapulothoracic articulation if the adjustable straps are pulled sufficiently tightly. However, a major shortcoming of the Rolyan hemi II arm sling is that it impinges the neurovascular contents of both axillae if placed tightly enough to elevate or retract the desired structures. This may adversely impact the brachial plexus and/or the subclavian artery or vein, causing numbness and/or swelling.

Another prior art device is the bi-shoulder wrap which heats tissues, thereby facilitating healing of bursitis or tendinitis. The bi-shoulder wrap, while providing therapeutic heat to the area of interest, has no effect on scapulothoracic mechanics unless the bi-shoulder wrap is structurally altered beyond the manufacturer's intended dimensions.

SUMMARY OF THE INVENTION

In one of its aspects this invention provides passive apparatus and methods for effortless and painless symmetrical scapulothoracic retraction and elevation to reduce inferolateral subluxation, as well as possible reduction of inferior glenohumeral subluxation, thereby permitting optimal posture and optimal dynamic kinematics in the shoulder area. The invention in its methods and apparatus aspects provides elevated scapulothoracic articulation in a comfortable manner by dispersing forces over the largest area of the patient's body and minimizing neurovascular compression.

The methods and apparatus of the invention have clinical applications in relieving painful and/or dysfunctional conditions associated with inferolateral distraction and scapulothoracic subluxation with or without inferior glenohumeral subluxation.

Clinical applications for this orthosis include thoracic kyphosis, treatment of occupationally related postural dysfunction, trapezius strain, pain disorder, spinal accessory neuropathy, hemiplegia or quadriplegia, cervical radiculopathy, myopathy, peripheral neuropathy (about the shoulder), and cumulative trauma disorder.

DESCRIPTION OF THE PREFERRED EMBODIMENTS AND BEST MODE KNOWN FOR PRACTICE OF THE INVENTION

Referring to FIGS. 1, 2, 4, 5, 7, and 15, the apparatus of the present invention, designated generally by reference number 20, comprises left and right thoracic panels, 21 and 22, respectively. The left and right thoracic panels, 21 and 22, are shaped to fit under the respective arms of a patient to cover respective sides of the patient's chest and back. Accordingly, each thoracic panel, 21 and 22, preferably defines a circular opening through which the patient's arm may be inserted. In addition, each of the thoracic panels, 21 and 22, preferably comprises vertically extending front and back edges, 23 and 24 respectively, defining lateral extremities of the panels.

The thoracic panels, 21 and 22, are preferably manufactured from a flexible, inelastic material such as nylon, Dacron, or other washable hypoallergenic material. For patient comfort, the interior surfaces of the panels, especially those that contact the patient's skin, may comprise or be covered with a terry cloth material.

Each thoracic panel, 21 and 22, comprises an anterior section and a posterior section. The anterior sections cover the patient's chest and impart anteroposterior and lateral to medial (frictional) forces in order to provide an adequate containment force to the anterior proximal sleeve to maintain correct position of use. In addition, the forces prevent deformation of the anterior sections of the thoracic panels, 21 and 22, which would occur by unopposed, lateral to medial pull on the posterior sections of the thoracic panels, 21 and 22. The anteroposterior forces imparted to the anterior upper chest at the pectoralis muscles against the ribs could pose an impediment to normal ease of respiration. Accordingly, the magnitude of the forces is maintained at a sufficiently low level.

The posterior sections of the thoracic panels, 21 and 22, cover the patient's back and impart minor posteroanterior force to the posterior thorax, ribs, and scapulae. The magnitude of the force is sufficient to maintain the apparatus against the patient's body wall.

Left and right sleeves, 25 and 26, are connected to the left and right thoracic panels, 21 and 22, respectively. The sleeves, 25 and 26, are adapted for covering the patient's shoulders and arms. Preferably, each sleeve comprises an upper or proximal portion 27 and a lower or distal portion 28. The upper portion 27 comprises a generally tubular section of material which can be positioned to cover the patient's shoulder. The upper portion 27 of each sleeve, 25 and 26, is connected to its respective thoracic panel, 21 and 22, at an oversewn seam 29. The upper portion 27 is preferably manufactured from an elastic material such as neoprene. To enhance the patient's comfort, the interior surfaces of the upper portions 27 of the sleeves, 25 and 26, especially those that contact the patient's skin, may comprise or be covered with a terry cloth material.

The upper portions 27 of the sleeves, 25 and 26, exerts a lateral to medial force, as well as a distal to proximal force, at the lateral portion of the upper arm. The medial portions of the sleeves, 25 and 26, encompass the superior and lateral portions of the axilla and impart a modest upward force. The upward force contributes to limb suspension, but is not strong enough to impinge upon neurovascular structures in the axilla. The upper portions 27 of the sleeves, 25 and 26, like the lower portions 28, enable the humerus to be better seated within the glenoid fossa of the scapula, in a similar embodiment.

The lower portion 28 of each sleeve, 25 and 26, comprises a generally tubular section of material which can be positioned to cover and apply pressure distal to the patient's biceps. The lower portions 28 of the sleeves, 25 and 26, are integrally formed with the upper portions 27 of the sleeves, 25 and 26. To enhance the patient's comfort, the interior surfaces of the lower portions 28 of the sleeves, 25 and 26, especially those that contact the patient's skin, may comprise or be covered with a terry cloth material.

Returning to FIG. 1, the lower portion 28 of each sleeve, 25 and 26, may comprise a lateral slit 33. The lateral slit 33 forms first and second flaps, 34 and 35 respectively, which function as a closure to enable the lower portions 28 of the sleeves, 25 and 26, to be adjusted to fit snugly around the patient's distal arm. Accordingly, an inner surface 36 of the first flap 34 may comprise a Velcro® patch 38 which mates with a Velcro patch on the outer surface 37 of the second flap 35, so that the inner surface 36 of the first flap 34 can be made to contact the outer surface 37 of the second flap 35 thereby securing each sleeve, 25 and 26, distal to the patient's biceps. Velcro closure permits releasability in the event that there is mild discomfort in a position of use. Alternatively, an inelastic closure can be used. Accordingly, the distal end 39 of the each sleeve, 25 and 26, cinches the distal part of the patient's arm at the tapering of the biceps.

Figure 1:
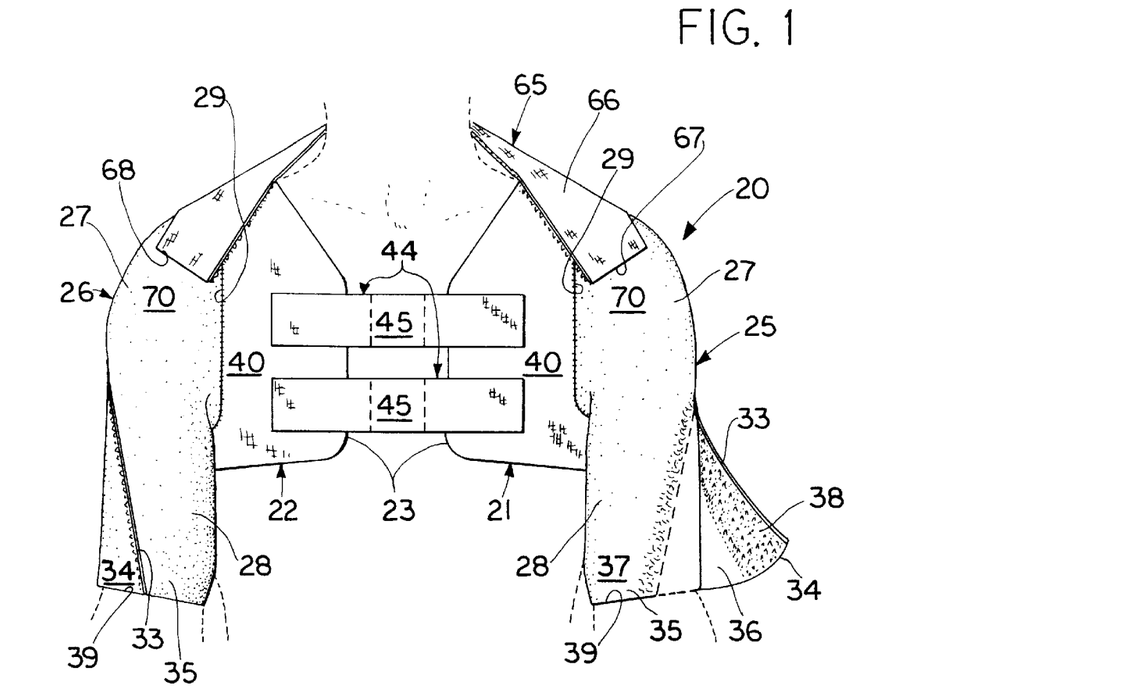
FIG. 1 is a front elevation view of a garment embodying aspects of the invention illustrated in position on a patient.

The lower portion 28 of each sleeve, 25 and 26, exerts a circumferential force distal to the distal biceps taper sufficient to prevent slippage of the arm distally by maintaining a grasp on the limb to pull it upward, but not so great as to cause neurovascular impingement. Only part of the total weight of the limb is borne by the distal end of the lower portion 28 of the sleeve, 25 or 26. In addition, there is a distal to proximal frictional force exerted on the tissues, further preventing slippage of the arm through the circumferential containment purchase at the distal bicep, while suspending the weight of the limb.

Figure 5:
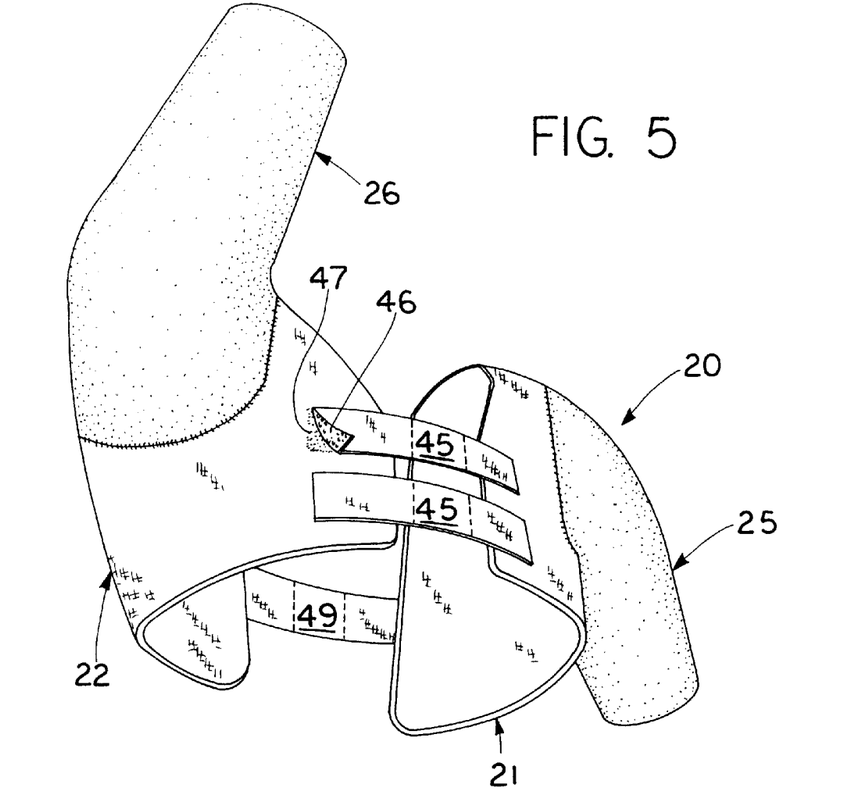
FIG. 5 is a perspective view of the garment illustrated in FIG. 1.

Front transversely extending means 44 are provided for adjustably pulling the front edges 23 of the left and right thoracic panels, 21 and 22, toward one another across the patient's chest. As depicted in FIG. 1, the front transversely extending means 44 comprises two partially elastic straps 45. However, the front transversely extending means may comprise one, three, or more straps 45. Each strap 45 comprises two partially elastic or inelastic portions 45A, each flanking a central elastic portion 45B, thereby permitting some chest expansion with breathing. The junction between the portions 45A and 45B may be oversewn for durability. As shown in FIG. 5, the ends of the straps 45 may comprise Velcro patches 46 which mate with Velcro patches 47 on the outer surfaces 40 of the thoracic panels, 21 and 22, to thereby connect the thoracic panels, 21 and 22, together. Accordingly, straps 45 of different lengths can be easily interchanged to provide a comfortable fit for the particular patient using the apparatus. For patient comfort, the surfaces of the straps 45 that contact the patient may be manufactured from or covered with a terry cloth material.

The straps 45 impart minor lateral to medial force from the upper portions of the sleeves, 25 and 26, through the anterior sections of the thoracic panels, 21 and 22, in a tangential surface vector. The straps 45 further connect the bilateral panels, maintain closure of the anterior sections of the thoracic panels, 21 and 22, against the chest wall, and prevent deformation of the upper portions of the sleeves, 25 and 26.

Figure 2:
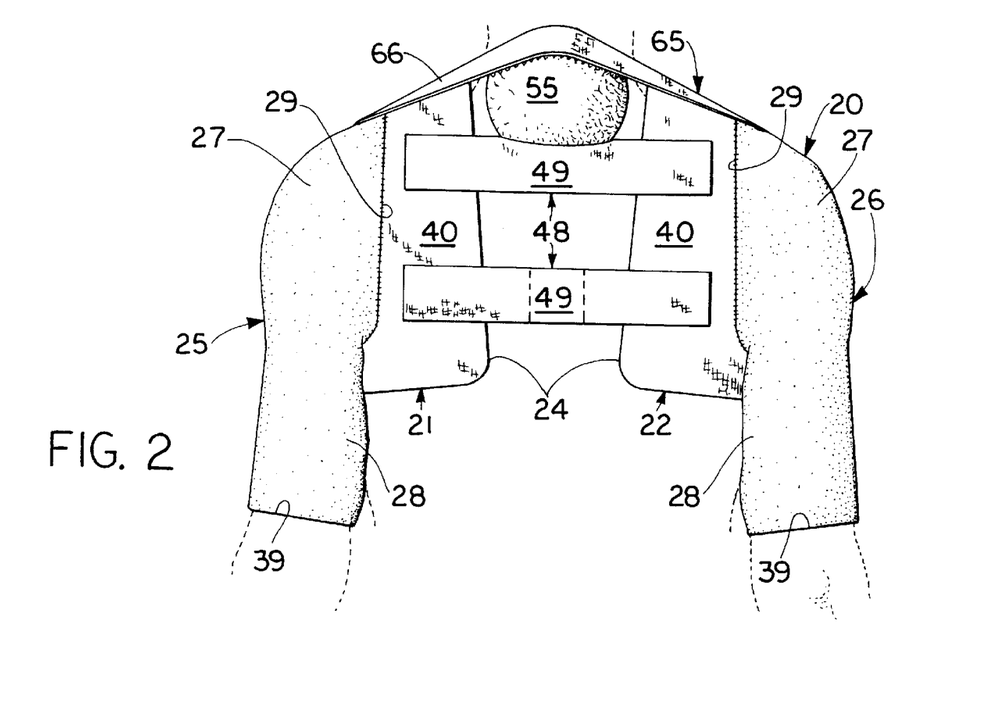
FIG. 2 is a rear elevation view of the garment of FIG. 1 on the same patient.

In addition, back transversely extending means 48 are provided for adjustably pulling the back edges 24 of the left and right thoracic panels, 21 and 22, toward one another across the patient's back. As depicted in FIG. 2, the back transversely extending means 48 comprises two inelastic straps 49. Those straps 49 are different from the straps 45 of the front transversely extending means 44, in that straps 49 are composed wholly of an inelastic material.

The straps 49 impart the majority of the lateral to medial retracting containment force connecting the bilateral lateral compressive forces against the upper arms at the deltoids and proximal humerii. The uppermost strap 49 provides an upward suspensory force to the inferior aspect of a bulbous disk 55, thereby causing an upward (superior directed) frictional force produced by the anterior surface of the disk 55 against the bones of the lower cervical and upper thoracic spine, as well as to the soft tissue of the paraspinal musculature and the uppermost scapulothoracic retractor musculature. Accordingly, the straps 49, along with panels 21 and 22, apply forces to the patient's deltoids and scapulae, and permit relaxation of scapulothoracic retractor muscles.

Figure 6:
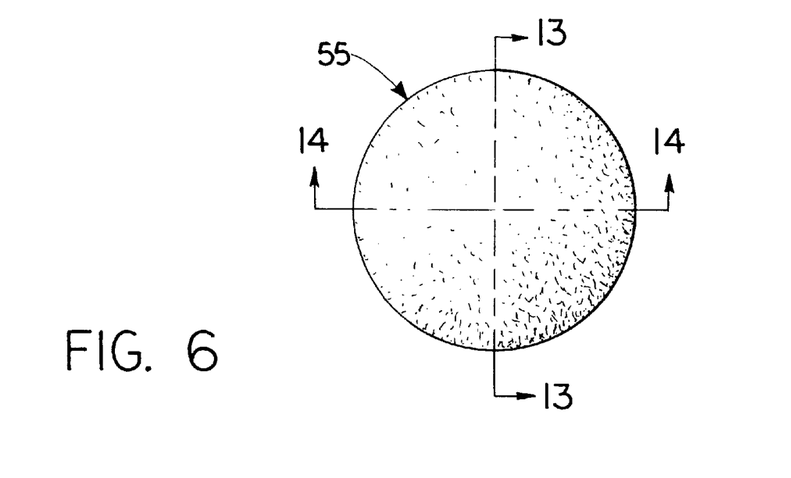
FIG. 6 is a front elevation view of the bulbous disk illustrated in FIG. 2.
Figure 7:
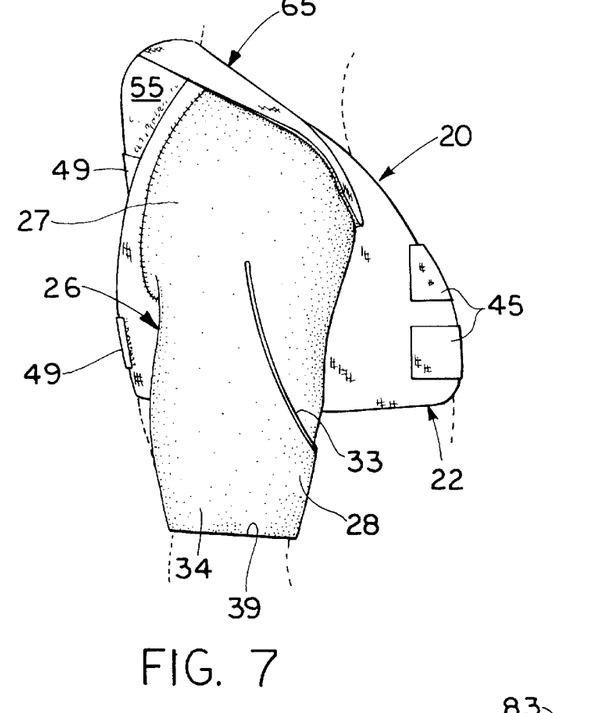
FIG. 7 is a side elevation view, looking at the patient's right side, of the garment illustrated in FIG. 1 shown with the arm flap in a closed configuration.
Figure 13:
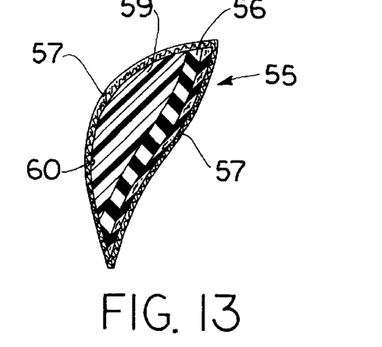
FIG. 13 is a vertical section through the bulbous disk of FIG. 6 taken along the 13—13 direction.
Figure 14:
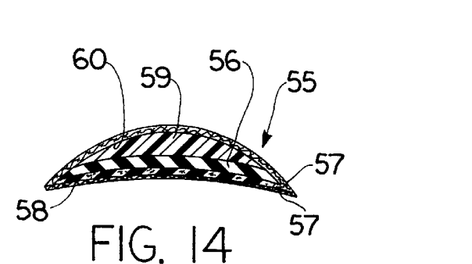
FIG. 14 is a horizontal section through the bulbous disk of FIG. 6 taken along the 14—14 direction.
Figure 15:
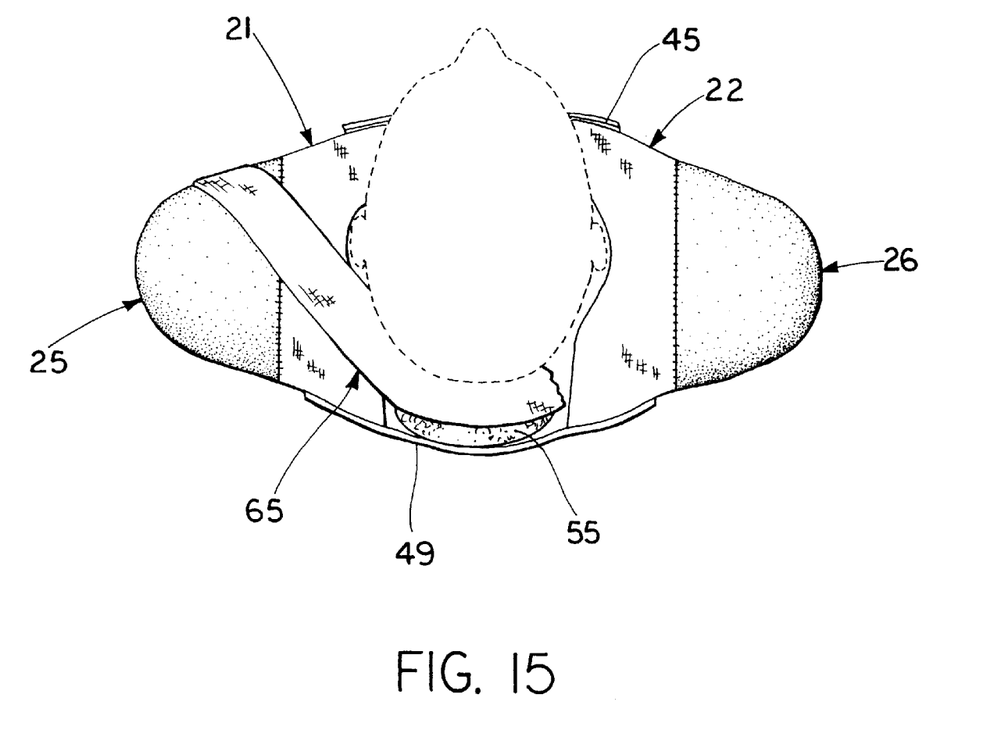
FIG. 15 is a top elevation view of the garment illustrated in FIG. 1.

The bulbous disk 55 is provided for contacting the rear of the patient's lower neck and upper back. The disk 55 serves as a fulcrum to increase the elevating force vector thereby distributing a downward force over the immobile cervicothoracic junction. The disk 55, as shown in FIG. 6, is preferably formed from a section of rubber padding 56. As shown in FIGS. 13 and 14, the rubber padding 56 may be shaped to provide a generally concave front surface 58 for contacting the patient's back. A dome 59 of elastomeric material is provided over the rubber padding 56. The rear surface 60 of the dome 59 is preferably shaped to have a convex surface to enhance the ability of the disk 55 to distribute the downward force over the cervicothoracic junction. The outer surfaces of the rubber padding 56 may be covered with a terry cloth material 57 to enhance the patient's comfort.

The disk 59 imparts a predominantly inferior directed force against the posterior lower cervical and upper thoracic vertebrae and paraspinal musculature, as well as, to a much lesser degree, the upper trapezii, rhomboids, and levator scapulae bilaterally. There will be some inferior frictional force represented by the tendency for the disk 55 to be pushed downward along the spine. This tendency will be minor and will be counteracted by the suspensory function of the uppermost strap 48. There could be a built-in variation of thickness or compressibility of the elastic elements of the disk 55, which would favor distribution of suspensory forces preferentially over the spine, and not the paraspinal soft tissues.

The means 65 for applying force to disk 55 imparts a posterosuperomedial force at the ends, 67 and 68, of strap 66, thereby bilaterally providing the main elevating force to the entire affected forequarter. This combined force is frictional at the anterior shoulder connecting in series with the distal to proximal forces created by the sleeve against the arm along its length. There is also a significant anteroposterior force against the deltoid and anterior shoulder which assists in retraction of the forequarter. The strap 66 creates a posterior directed force over the clavicle, with a smaller component of downward force against the superior scapular area. The medial portion of the strap 66 sits affixed to the posterosuperior portion of the disk 55. Forces from the ends, 67 and 68, of strap 66 are directed towards each other in series. This force contributes in a minor way to retracting the scapulae and shoulder girdles backward on the thorax toward each other. More significantly, this force creates the forces which produce scapulothoracic elevation, lifting the forequarters up along the thorax toward the neck. Additionally, there is an inferior directed force placed onto the posterosuperior portion of disk 55, which will be translated to the body, as described above. This force is counteracted by the uppermost strap 48, thereby preventing inferior slippage of the disk 55 on the neck and upper back.

The apparatus 20 further comprises a means 65 for applying force to the bulbous disk 55 in a downward and forward direction, thereby applying a spreading force over the patient's neck and back. As shown, the means 65 for applying force to the disk 55 preferably comprises a strap 66 having first and second ends, 67 and 68, respectively. The ends, 67 and 68, are connected to the front surfaces 70 of the upper portions 27 of the sleeves, 25 and 26, preferably by Velcro patches on the ends, 67 and 68, of the strap 66 which mate with corresponding Velcro patches on the front surfaces 70 of the upper portions 27 of the sleeves, 25 and 26. The strap 66 extends behind the neck of the patient and over the disk 55. Accordingly, the strap 66 exerts a force on the disk 55 which maintains the disk 55 in place about the patient's rear, lower neck and upper back. Additionally, as shown, the back transversely extending means 48 may exert an additional upward suspensory force upon the disk 55.

Figure 8:
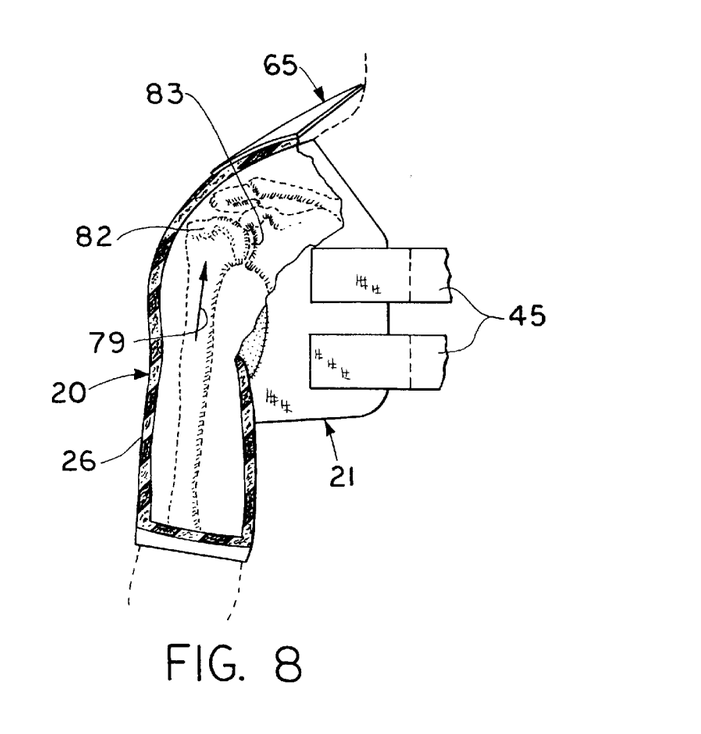
FIG. 8 is a cut-away, front elevation view of the right side of the garment illustrated in FIG. 1 illustrating the elevation of the humerus into the glenoid fossa.
Figure 9:
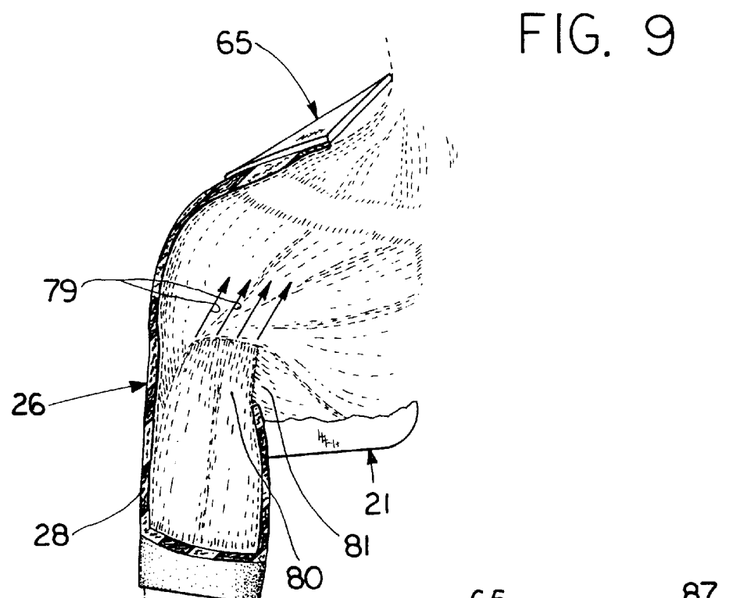
FIG. 9 is a cut-away, front elevation view of the right side of the garment illustrated in FIG. 1 illustrating the forces which are dispersed upwardly across the deltoid and pectorals.
Figure 11:
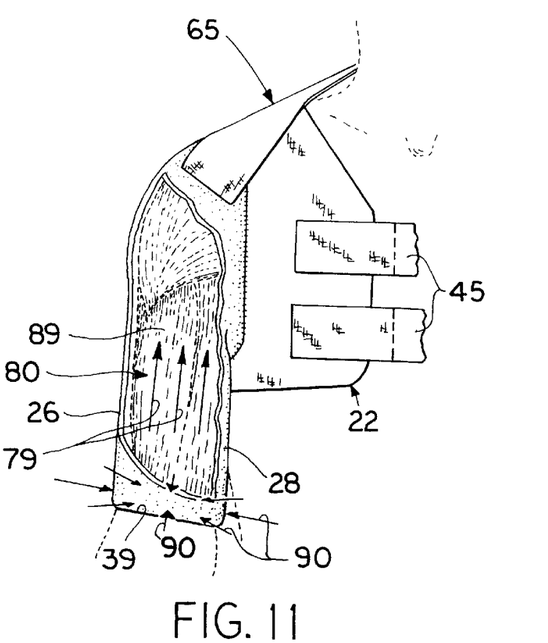
FIG. 11 is a cut-away, front elevation view of the right side of the garment illustrated in FIG. 1 illustrating that the sleeve cinches the distal part of the patient's arm at the tapering of the biceps.
Figure 12:
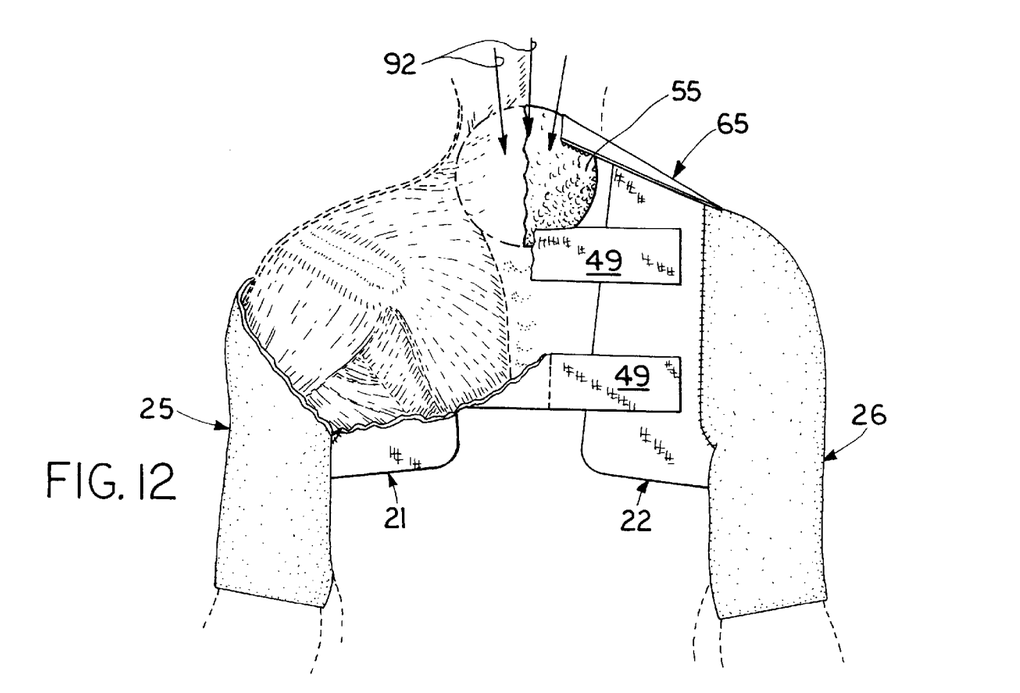
FIG. 12 illustrates the downwardly and inwardly directed forces applied by the bulbous disk to the posterior spine at the cervico-thoracic junction.

The apparatus 20 provides elevated scapulothoracic articulation in a comfortable manner by dispersing forces over the largest area of the patient's body while minimizing neurovascular compression. As shown in FIG. 12, the bulbous disk 55 and means 65 exert downwardly and inwardly directed forces 92 to the posterior spine at the cervicothoracic junction. Further, as depicted in FIG. 11, the distal end 39 of sleeve 26 applies forces 90 to the distal part of the patient's upper arm 89 at the tapering of the biceps 80. Consequently, forces 79 are applied to the patient's right arm which produce axial longitudinal elevation of the humerus toward the scapula. As shown in FIGS. 8 and 9, the lower portion 28 of the sleeve 26 functions to distribute suspending forces 79 to the distal part of the upper arm 89 as well as the axilla 81. Accordingly, the suspending forces 79 elevate the humerus 82 into the glenoid fossa 83, thereby minimizing brachial plexus and axillary blood vessel traction and shoulder capsular distraction. Although not shown, an analogous distribution of suspending forces is applied to the left side of the patient.

Figure 10:
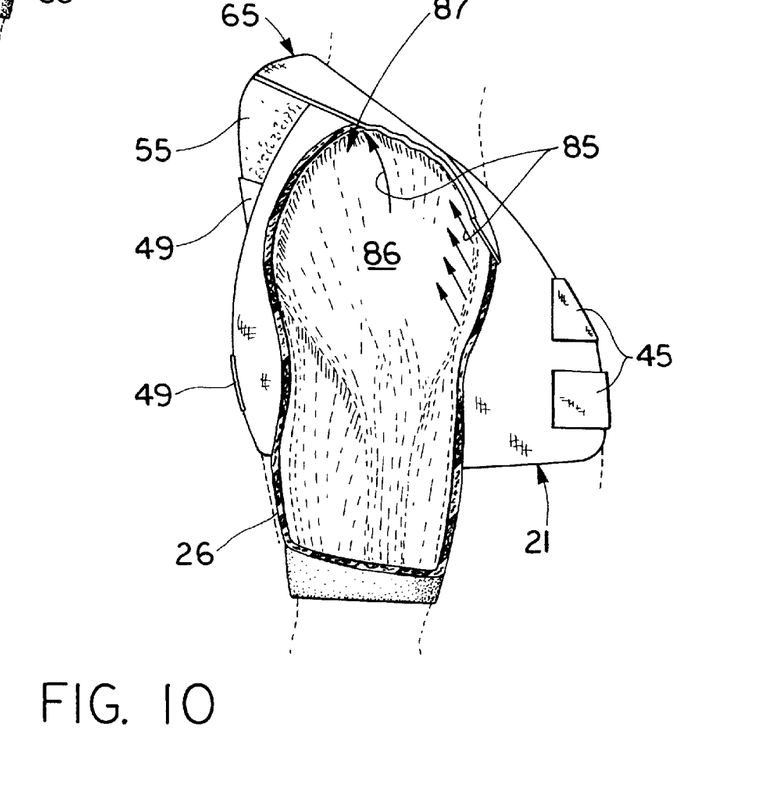
FIG. 10 is a cut-away, side elevation view, looking at the patient's right side, of the garment illustrated in FIG. 1 illustrating the forces exerted on the right shoulder to elevate the right shoulder and pull the right shoulder toward the left shoulder.

In addition, as shown in FIG. 10, spreading forces 85 are applied over the patient's anterior shoulder. These forces 85 effectively produce scapulothoracic elevation and retraction, decreasing traction on scapulothoracic elevator and retractor musculature. These forces 85 are counterbalanced by the better tolerated forces directed upon more immobile and rigid tissues. Although FIG. 10 only illustrates the forces applied to the patient's right side, analogous forces are also applied to the patient's left side. These forces 85 elevate the scapulae 86 and urge the shoulders 87 backward towards each other.

Mostly, the lateral to medial forces created by the straps 48 pull the shoulder girdles into retraction. The lateral to medial forces from one sleeve connect in series to the lateral to medial force imparted by the posterior section of the thoracic panels, 21 and 22, to the strap 48 and then to the contralateral, lateral to medial forces created by the same apparatus components of the other side of the apparatus.

Figure 3:
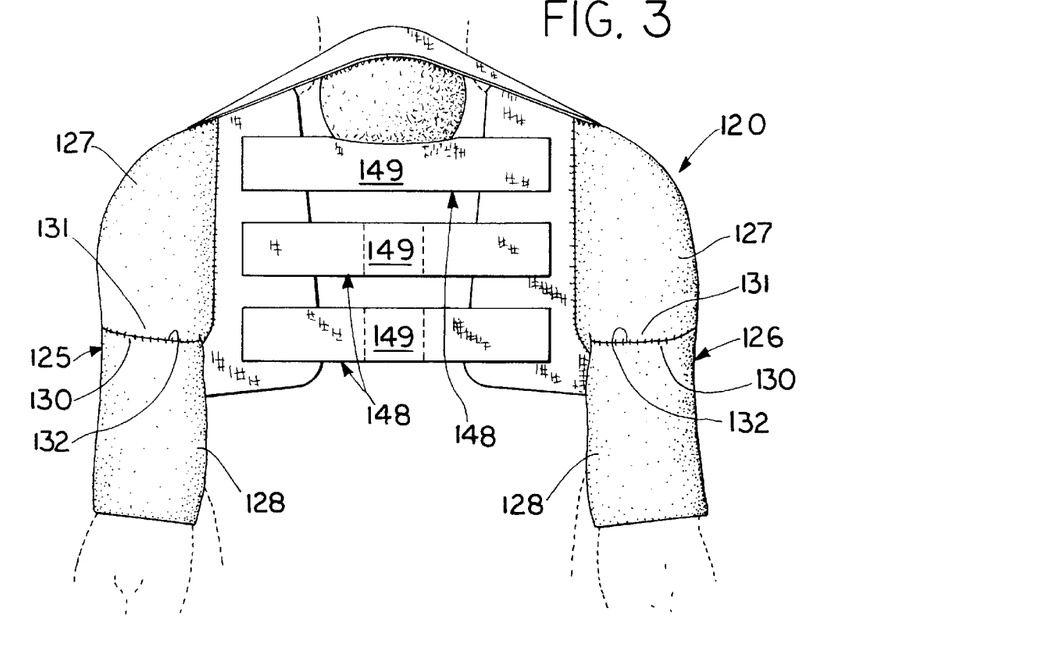
FIG. 3 is a rear elevation view of a second embodiment of a garment in accordance with the present invention illustrated in position on a patient.
Figure 4:
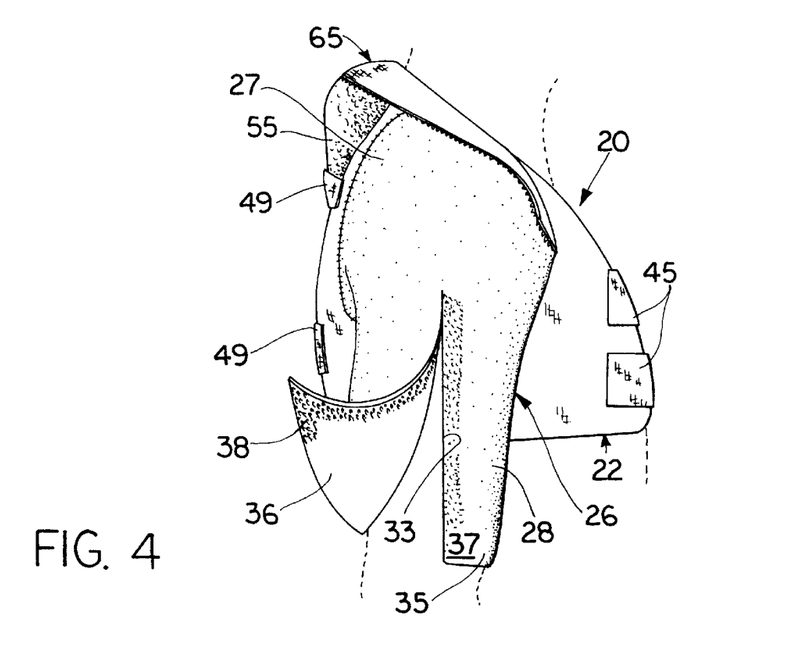
FIG. 4 is a side elevation view, looking at the patient's right side, of the garment illustrated in FIG. 1 shown with the arm flap in an open configuration.

In an alternative embodiment, as shown in FIG. 3, an apparatus 120 can be utilized. Apparatus 120 is similar to apparatus 20 described above except that the proximal ends 130 of the lower portions 128 of the sleeves, 125 and 126, are connected to the distal ends 131 of the upper portions 127 of the sleeves, 125 and 126, at a seam 132. The lower portions 128 may be constructed of inelastic material. In addition, the back transversely extending means 148 comprises three straps 149. However, the back transversely extending means 148 may comprise any number of straps 149, depending on the particular application.

In operation, the right thoracic panel 22 is positioned under the patient's right arm with the front edge 23 adjacent the patient's chest and the back edge 24 adjacent the patient's back. The left thoracic panel 21 is then positioned under the patient's left arm in an analogous manner.

The patient's right arm is then positioned within the right sleeve 26 with the upper portion 27 of the right sleeve 26 about the patient's right shoulder. The right sleeve 26 is then connected to the right thoracic panel 22. If the lower portion 28 of the sleeve 26 comprises a slit 33, the flaps, 34 and 35, are secured to one another to insure that the lower portion 28 of the sleeve 26 fits snugly about the patient's distal arm. The patient's left arm is then positioned within the left sleeve 25 and the left sleeve 25 connected to the left thoracic panel 21 in an analogous manner.

The back edges 24 of the left and right panels, 21 and 22, are then pulled towards one another across the patient's back with the application of a substantially constant force. The back transversely extending means 48 are then used to maintain the panels, 21 and 22, in an adjustably approximated position about the patient's back.

The front edges 23 of the left and right panels, 21 and 22, are then pulled towards one another across the patient's chest by applying a gentle, constant force. These forces imparted by the extending means 44 are intended to be trivial, so as not to impede breathing or counteract the therapeutic benefit of the retracting forces imparted by transversely extending means 48. The front transversely extending means 44 are used to maintain the panels, 21 and 22, in position about the patient's chest.

The bulbous disk 55 is then positioned in contact with the rear of the patient's lower neck and upper back. When the bulbous disk 55 shown in FIGS. 6, 13, and 14 is used, the disk 55 is positioned with the concave front surface 58 of the disk 55 adjacent the patient and the convex rear surface 60 directed away from the patient's back.

The means 65 for applying force to the bulbous disk 55 is then secured to the apparatus 20. As shown in the figures, one end 67 of strap 66 is secured to the upper portion 27 of either the left sleeve 25 or right sleeve 26. The strap 66 is then passed behind the patient's neck so that the strap 66 abuts against the disk 55. The second end 68 of the strap 66 is then secured to the upper portion 27 of the other sleeve, 26 or 25, while the patient's shoulder girdles are assisted into an optimally elevated position. The transversely extending means 48 may be positioned to effect optimal scapulothoracic retraction while the patient is assisted into an optimally retracted position.

Accordingly, it should be apparent that the apparatus of the present invention is useful in a wide range of applications. For example, the apparatus can be used to accelerate healing of, relieve the symptoms associated with, or prevent biomechanical or physiologic complications due to a strained, torn, inflamed, or degenerated levator scapula, rhomboideus muscle, trapezius, deltoid, or supraspinatus; to treat, relieve the symptoms associated with, or prevent biomechanical or physiologic complications due to a levator scapula, rhomboideus muscle, trapezius, deltoid, supraspinatus, clavicle, scapula, or thoracic vertebra from which a tumor has been resected; to accelerate healing of, relieve the symptoms associated with, or prevent biomechanical or physiologic complications due to a fractured or degenerated clavicle, scapula, or thoracic vertebra; to accelerate healing of, relieve the symptoms associated with, or prevent biomechanical or physiologic complications due to an injured central or peripheral nerve; or to restore physiologic alignment of the shoulder at rest or during light activity.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

I claim:

1. Garment apparatus for therapeutically applying force to a patient's upper torso and cervical region, comprising:
   (a) a pair of flexible form-fitting panels adapted to fit under the arms of a patient and to cover respective sides of the patient's chest and back, said panels having vertically extending edges defining lateral extremities of said panels at the patient's chest and back, said edges being spaced from one another;
   (b) a pair of sleeves having upper portions adapted for covering said patient's shoulders and connected to said panels by seams running upwardly along said patient's chest and back, having downwardly extending lower tubular portions adapted for receiving said patient's arms therein, said tubular portions having a vertical slit and being adapted for overlapping adjustable fitting about a patient's distal biceps;
   (c) transversely extending means operatively connected to said form-fitting panels for adjustably maintaining said panels against said patient's chest;
   (d) a partly elastomeric and partly foam rubber bulbous disk for contacting the rear of the patient's lower neck and upper back and for applying a spreading force over the patient's neck and back, concentrated over the spine;
   (e) strap means connected to front surfaces of said sleeve upper portions and contacting said disk, said strap means being adapted for extending behind the neck of said patient, for applying force in a downward and forward direction to said disk and hence to said patient's neck and back as well as in an upward and backward direction to said patient's shoulder girdles and upper extremities;
   (f) transversely extending means for adjustably pulling said panels towards one another across said patient's back.

2. The garment apparatus of claim 1 wherein said sleeves are elastomeric.

3. The garment apparatus of claim 1 wherein said panels are fabric.

4. The garment apparatus of claim 1 wherein said panels have gripping means on one surface thereof adapted for pressure sensitive adherence to said pulling means.

5. The garment apparatus of claim 1 wherein said transversely extending means for adjustably pulling said panels towards one another across said patient's chest and back are generally rectangular fabric straps.

6. The garment apparatus of claim 1 wherein said transversely extending means for adjustably pulling said panels towards one another across said patient's back are fabric panels.

7. The garment apparatus of claim 6 further comprising pressure sensitive adhesive means on said fabric panels for releasably adjustably securing said rectangular fabric panels to said sleeves.

8. The garment apparatus of claim 7 further comprising pressure sensitive adhesive means on said fabric panels for releasably adjustably securing said fabric panels to said form-fitting panels.

9. The garment apparatus of claim 6 further comprising pressure sensitive adhesive means on said fabric panels for releasably adjustably securing said rectangular fabric panels to said form fitting panels.

10. The garment apparatus of claim 9 further comprising pressure sensitive adhesive means on said fabric panels for releasably adjustably securing said fabric panels to said form-fitting panels.

11. The garment apparatus of claim 10 wherein said pressure sensitive adhesive means on said fabric panels for releasably adjustably securing said fabric panels to said form-fitting panels and said pressure sensitive adhesive means for releasably adjustably securing said fabric panels to said form-fitting panels are the same materials.

12. The garment apparatus of claim 1 wherein said elastomeric bulbous disk has an outer convex surface adapted for contact by said strap means.

13. The garment apparatus of claim 1 wherein said elastomeric bulbous disk has an inner concave surface adapted for contacting said patient's lower neck and upper back.

14. The garment apparatus of claim 1 further comprising pressure sensitive adhesive means on said strap means for releasably adjustably securing said strap means to said sleeves.

15. The garment apparatus of claim 14 further comprising pressure sensitive adhesive means on said transversely extending means for releasably adjustably securing said transversely extending means to said form-fitting panels.

16. The garment apparatus of claim 1 further comprising pressure sensitive adhesive means on said strap means for releasably adjustably securing said strap means to said form fitting panels.

17. The garment apparatus of claim 16 further comprising pressure sensitive adhesive means on said transversely extending means for releasably adjustably securing said transversely extending means to said form-fitting panels.

18. A method for therapeutically applying compressive force to a patient's upper torso including the patient's levator scapula, rhomboideus muscle, trapezium, deltoid, clavicle, scapula, thoracic vertebra, and biceps to accelerate healing of at least one of said levator scapula, rhomboideus muscle, trapezium, deltoid, supraspinatus, clavicle, scapula, thoracic vertebra, central nerve, and peripheral nerve comprising:

(a) fitting a pair of flexible form-fitting panels under the arms of a patient in a manner to cover respective sides of the patient's chest and back, said panels having vertically extending edges defining lateral extremities of said panels at the patient's chest and back, with said edges being spaced from one another;

(b) covering the patient's shoulders and arms with upper portions of a pair of sleeves connected to said panels by seams running upwardly along said patient's chest and back, and covering the patient's arms with downwardly extending lower tubular portions of the sleeves by receiving said patient's arms therein with said tubular portions being vertically slit;

(c) overlapping the vertical slit lower tubular portions of the sleeves receiving said patient's arms therein to overlappingly adjustably fit about a patient's biceps and thereby apply pressure distal to the patient's biceps;

(d) pulling said panels towards one another across said patient's chest;

(e) positioning an elastomeric bulbous disk contacting the rear of the patient's neck to spread force applied to the exterior of said disk over the patient's neck and upper back;

(f) positioning strap means connected to front surfaces of said sleeve upper portions behind the neck of said patient to apply force in a forward direction to said disk and hence to said patient's levator scapula, rhomboideus muscle, trapezius, and thoracic vertebra; and (g) adjustably pulling said panels towards one another across said patient's back thereby to apply compressive force to the patient's deltoid, scapula, and biceps.

* * * * *